(12) United States Patent
Chung et al.

(10) Patent No.: US 8,691,195 B2
(45) Date of Patent: Apr. 8, 2014

(54) PEPTIDE HAVING ACTIVITY OF TRANSFORMING GROWTH FACTOR AND PRODUCTION METHOD THEREFOR

(75) Inventors: Young Ji Chung, Yongin-si (KR);
Young Deug Kim, Siheung-si (KR);
Eun Mi Kim, Gunpo-si (KR); Jeong Jin Choi, Seoul (KR); Jun Young Choi, Gunpo-si (KR)

(73) Assignee: Caregen Co., Ltd., Gunpo-Si, Gyeonggi-Do (KR)

( * ) Notice: Subject to any disclaimer, the term of this patent is extended or adjusted under 35 U.S.C. 154(b) by 0 days.

(21) Appl. No.: 13/264,290

(22) PCT Filed: Apr. 14, 2009

(86) PCT No.: PCT/KR2009/001918
§ 371 (c)(1),
(2), (4) Date: Dec. 27, 2011

(87) PCT Pub. No.: WO2010/119997
PCT Pub. Date: Oct. 21, 2010

(65) Prior Publication Data
US 2012/0114577 A1 May 10, 2012

(30) Foreign Application Priority Data
Apr. 14, 2009 (KR) .................. 10-2009-0032052

(51) Int. Cl.
*A61K 8/64* (2006.01)
*C07K 7/08* (2006.01)

(52) U.S. Cl.
CPC ..................................... *A61K 8/64* (2013.01)
USPC ............ 424/62; 530/328; 530/327; 514/21.7; 514/1.9; 514/16.7

(58) Field of Classification Search
None
See application file for complete search history.

(56) References Cited

U.S. PATENT DOCUMENTS 5,436,228 A     7/1995   Postlethwaite et al.
6,500,920 B1 *  12/2002  Haung .......................... 530/328

FOREIGN PATENT DOCUMENTS

KR    20090132815 A    12/2009
KR    20090132911 A    12/2009
WO    WO 2008/130082 A1 *  10/2008

* cited by examiner

*Primary Examiner* — Jean Witz
*Assistant Examiner* — Mindy Newman
(74) *Attorney, Agent, or Firm* — Clark & Elbing LLP

(57) ABSTRACT

The present invention relates to a transforming growth factor-beta (TGF-β)-mimicking peptide containing a particular amino acid sequence and a composition for preventing or treating TGF-β-effective disorders or conditions using the same. The peptide of the present invention may be much higher stability than natural-occurring TGF-β and improve drawbacks caused by high molecular weight of natural-occurring TGF-β. The peptide of this invention can be advantageously applied to treatment or improvement of TGF-β-effective disorders or conditions and have excellent efficacies on skin whitening and wrinkle improvement.

7 Claims, 13 Drawing Sheets

Fig. 1

| Protein | Source | 1        10        20        30        40        50 |
|---------|--------|------------------------------------------------------|
| TGF-β1  | human  | ALDTNYCFSST--EKNCCVRQLYIDFRKDLGWKWIHEPKGYHANFCLGPCPY |
| TGF-β3  | human  | ALDTNYCFRNL--EENCCVRPLYIDFRQDLGWKWVHEPKGYYANFCSGPCPY |

| Protein | 51        60        70        80        90        100        110 |
|---------|-------------------------------------------------------------------|
| TGF-β1  | IWSLDTQYSKVLALYNQHNPGASAAPCCVPQALEPLPIVYYVGRKPKVEQLSNMIVRSCKCS |
| TGF-β3  | LRSADTTHSTVLGLYNTLNPEASASPCCVPQDLEPLTILYYVGRTPKVEQLSNMVVKSCKCS |

Sequence 1

PEPTIDE HAVING ACTIVITY OF TRANSFORMING GROWTH FACTOR AND PRODUCTION METHOD THEREFOR

CROSS-REFERENCE TO RELATED APPLICATIONS

This application is the U.S. national stage filing under 35 U.S.C. §371 of international application PCT/KR2009/001918, filed Apr. 14, 2009, which claims benefit of Korean Patent Application 10-2009-0032052, filed Apr. 14, 2009.

BACKGROUND OF THE INVENTION

1. Field of the Invention

The present invention relates to peptides having activities of transforming growth factor-beta (TGF-β) and their uses.

2. Description of the Related Art

Transforming growth factor-beta (TGF-β) is a group of polypeptide growth factors regulating cell differentiation and growth. This group also includes Mulleria inhibitors (Cate et al, *Cell*, 45: 685-698 (1986)), inhibins (Mason et al., *Nature*, 318: 659-663 (1985)), and proteins derived from transcripts of DPP-C (decapentaplegic gene complex) in *Drosophila* (Padgett et al., *Nature*, 325: 81-84 (1987)). TGF-β consists of two similar disulfide-linked subunits each having a molecular weight of 13,000 daltons (Assoian et al, *J. Biol. Chem.*, 258: 7155-7160 (1983); Frolik et al, *Proc. Natl. Acad. Sci. USA*, 80: 3676-3680 (1983); Frolik et al., *J. Biol. Chem.* 260: 10995-11000 (1984)). TGF-βs have been purified from several tissues, including placenta (Frolik et al., *Nature*, 325: 81-84 (1983)), human platelet (Childs et al, *Proc. Natl. Acad. Sci. USA*, 79: 5312-5316 (1982); Assioan et al., *J. Biol. Chem.*, 258: 7155-7160 (1983)), kidney (Roberts et al., *Biochemistry*, 22: 5692-5698 (1983)), and bovine demineralized bone (Seyedin et al., *Proc. Natl. Acad. Sci. USA*, 82: 119-123 (1985)). TGF-β is able to increase anchorage-independent growth of normal rat kidney fibroblast in the presence of 10% serum and epidermal growth factors (Roberts et al, *Proc. Natl. Acad. Sci. USA*, 78: 5339-5343 (1981); Roberts et al., *Nature*, 295: 417-419 (1982); Twardzik et al, *J. Cell Biochem.*, 28: 289-297 (1985)), and to induce colonization of AKR-2B fibroblasts in only 10% serum (Tucker et al., *Cancer Res.*, 43: 1518-1586 (1983)). In addition, it has been reported that TGF-β may cause differentiation of muscle mesenchymal cells and generation of cartilage-specific macromolecules in fetal rats (Seyedin et al., *J. Biol. Chem.*, 261: 5693-5695 (1986)).

In contrast to various effects on cell proliferation, it has been observed that not only functional proteins having similar activities of TGF-β isolated from African green monkey kidney epithelial cells (BSC-1) but TGF-β purified from human platelet could inhibit the growth of certain cells during cell culture (Tucker et al., *Science*, 226: 705-707 (1984)). TGF-β was also found to inhibit the growth of a few human tumor cells (Roberts et al., *Proc. Natl. Acad. Sci. USA*, 82: 119-123 (1985)). These inhibitory or stimulatory effects of TGF-β have been reported to be dependent on several factors related to cell morphology and cell physiological conditions (Spon et al., *Science*, 232: 534 (1986)).

TGF-β cDNA clones were isolated from human (Derynck et al, *Nature*, 316: 701-705 (1985)), mouse (Derynck et al., *J. Biol. Chem.*, 261: 4377-4379 (1986)), and simian virus 40 (Sharples et al., *DNA*, 6: 239-244 (1987)). By analyzing their DNA sequences, it was reported that TGF-β is synthesized as a large precursor polypeptide and then spliced to produce a TGF-β monomer. The amino acid sequence between aforementioned TGF-β precursor proteins was found to have much higher homology.

Recently, it has been identified that a protein isolated from bovine demineralized bone is related to TGF-β (Seyedin et al., *J. Biol. Chem*, 262: 1946-1949 (1987)). The protein has also been isolated from other species including porcine blood platelets (Cheifetz et al., *Cell*, 48: 409-415 (1987)), human prostatic adenocarcinoma cell line PC-3 (Ikeda et al., *Biochemistry*, 26: 2406-2410 (1987)), and human glioblast cell (Wrann et al., *EMBO J*, 6: 1633-1636 (1987)). Since the amino acid sequence of this protein is partially homologous to that of TGF-β, it was named as TGF-β2. Thus, the TGF-βs isolated from human (Derynck et al., *Nature*, 316: 701-705 (1985)), mouse (Derynck et al., *J. Biol. Chem.*, 261: 4377-4379 (1986)), and simian virus 40 (Sharples et. al., *DNA*, 6: 239-244 (1987)) were renamed as TGF-β1.

Throughout this application, various patents and publications are referenced, and citations are provided in parentheses. The disclosure of these patents and publications in their entities are hereby incorporated by references into this application in order to more fully describe this invention and the state of the art to which this invention pertains.

DETAILED DESCRIPTION OF THIS INVENTION

TGF-β is a highly active protein. Unfortunately, its utilization and application have not yet become widened because of its poor expression, high production cost and short half-life. For developing peptides having actions identical to natural-occurring TGF-β, and having more significant characteristics such as activity, skin penetration and stability than natural-occurring TGF-β, the present inventors have made a variety of human TGF-β-derived peptides and screened. As a result, the present inventors have discovered a peptide having excellent characteristics described above on the basis of the amino acid sequence of natural-occurring TGF-β, eventually accomplishing the present invention.

Accordingly, it is one object of this invention to provide a TGF-β (transforming growth factor-beta)-mimicking peptide.

It is another object of this invention to provide a composition for preventing or treating TGF-β-effective disorders or conditions.

It is still another object of this invention to provide a method for prevention or treatment of TGF-β-effective disorders or conditions.

Other objects and advantages of the present invention will become apparent from the following detailed description together with the appended claims and drawings.

In one aspect of this invention, there is provided a TGF-β (transforming growth factor-beta)-mimicking peptide comprising the amino acid sequence represented by SEQ ID NO:1

TGF-β is a highly active protein. Unfortunately, its utilization and application have not yet become widened because of its poor expression, high production cost and short half-life. For developing peptides having actions identical to natural-occurring TGF-β, and having more significant characteristics such as activity, skin penetration and stability than natural-occurring TGF-β, the present inventors have made a variety of human TGF-β-derived peptides and screened. As a result, the present inventors have discovered a peptide having excellent characteristics described above on the basis of the amino acid sequence of natural-occurring TGF-β.

The peptide of the present invention fundamentally includes the human TGF-β-derived amino acid sequence.

According to a preferable embodiment, a cell adhesion amino acid sequence is further linked to a N-terminal or C-terminal of the present peptide, and more preferably, to the N-terminal of the present peptide. The cell adhesion amino acid sequence functions to improve TGF-β activities of the peptide of the present invention.

The cell adhesion amino acid sequence useful in the present invention may include any cell adhesion amino acid sequence known to those ordinarily skilled in the art. Preferably, the cell adhesion amino acid sequence is RGD(Arg-Gly-Asp), RGDS(Arg-Gly-Asp-Ser), RGDC(Arg-Gly-Asp-Cys), RGDV(Arg-Gly-Asp-Val), RGES(Arg-Gly-Glu-Ser), RGDSPASSKP(Arg-Gly-Asp-Ser-Pro-Ala-Ser-Ser-Lys-Pro), GRGDS(Gly-Arg-Gly-Asp-Ser), GRADSP(Gly-Arg-Ala-Asp-Ser-Pro), KGDS(Lys-Gly-Asp-Ser), GRGDSP(Gly-Arg-Gly-Asp-Ser-Pro), GRGDTP(Gly-Arg-Gly-Asp-Thr-Pro), GRGES(Gly-Arg-Gly-Glu-Ser), GRGDSPC(Gly-Arg-Gly-Asp-Ser-Pro-Cys), GRGESP(Gly-Arg-Gly-Glu-Ser-Pro), SDGR(Ser-Asp-Gly-Arg), YRGDS(Tyr-Arg-Gly-Asp-Ser), GQQHHLGGAKQAGDV (Gly-Gln-Gln-His-His-Leu-Gly-Gly-Ala-Lys-Gln-Ala-Gly-Asp-Val), GPR(Gly-Pro-Arg), GHK(Gly-His-Lys), YIGSR(Tyr-Ile-Gly-Ser-Arg), PDSGR(Pro-Asp-Ser-Gly-Arg), CDPGYIGSR(Cys-Asp-Pro-Gly-Tyr-Ile-Gly-Ser-Arg), LCFR(Leu-Cys-Phe-Arg), EIL(Glu-Ile-Leu), EILDV(Glu-Ile-Leu-Asp-Val), EILDVPST(Glu-Ile-Leu-Asp-Val-Pro-Ser-Thr), EILEVPST (Glu-Ile-Leu-Glu-Val-Pro-Ser-Thr), LDV(Leu-Asp-Val) or LDVPS(Leu-Asp-Val-Pro-Ser), and most preferably, RGD (Arg-Gly-Asp). The RGD sequence is a sequence to be selected from a matrix protein, fibronectin.

Even though the peptides of this invention per se have higher stability than natural-occurring TGF-β, its modification enables to have much higher stability. According to a preferable embodiment, the peptides of this invention have at their N-terminal or C-terminal a protection group selected from the group consisting of acetyl group, fluorenyl methoxy carbonyl group, formyl group, palmitoyl group, myristyl group, stearyl group, polyethylene glycol (PEG) and an amino acid. The protection groups are also responsible for the stability of the present peptides.

More preferably, the protection group is an amino acid, much more preferably Gly or Ala, and most preferably, Gly. Using an amino acid as a protection group, the number of amino acid residue is in a range of preferably 1-3, more preferably 1-2, and most preferably, 1.

The term used herein "stability" refers to in vivo stability and storage stability (e.g., storage stability at room temperature) as well.

According to a preferable embodiment, the cell adhesion amino acid sequence is linked to N-terminal or C-terminal of SEQ ID NO:1, SEQ ID NO:2 or SEQ ID NO:3, more preferably N-terminal, and then, the above-described protection group is linked to.

An exemplified example of the present peptide is described in SEQ ID NO:2.

The term used herein "peptide" refers to a linear molecule formed by linking amino acid residues through peptide bonds.

The peptides of the invention may be prepared by conventional chemical synthesis processes known to one of skill in the art, in particular, solid-phase synthesis techniques (Merrifield, *J. Amer. Chem. Soc.*, 85: 2149-54 (1963); Stewart, et al., *Solid Phase Peptide Synthesis*, 2nd. ed., Pierce Chem. Co.: Rockford, 111 (1984)).

The present peptides not only possess excellent activities of naturally occurring human TGF-β but also show higher stability to physiochemical factors such as acid and alkali. The peptides of this invention having significant long-term storage stability may be advantageously applied to products requiring long-term storage such as drugs, quasi-drugs, cosmetics and tooth/mouth cleaning or caring products.

In another aspect of this invention, there is provided a composition for preventing or treating TGF-β-effective disorders or conditions, comprising as an active ingredient the present peptide having activities of TGF-β.

In still another aspect of this invention there is provided a method for prevention or treatment of TGF-β-effective disorders or conditions, comprising administering to a subject in need thereof a composition which comprises as an active ingredient the present peptide having activities of TGF-β.

Since the present composition contains the peptide of this invention described above as active ingredients, the common descriptions between them are omitted in order to avoid undue redundancy leading to the complexity of this specification.

The peptide utilized as an active ingredient in the present invention has an activity or function of natural-occurring TGF-β by being applied to a living body because of its TGF-β activity. The term "TGF-β activity" used herein refers to any and all activities of natural-occurring TGF-β known to one of skill in the art, for example, including promotion of cell growth and division. The peptide of the present invention may exert various biological activities of natural-occurring TGF-β because it is produced to mimic natural-occurring TGF-β activities.

Since the present peptide has actions identical to natural-occurring TGF-β, and shares similar physiological characteristics with natural-occurring TGF-β, it may be utilized to prevent or treat TGF-β-effective disorders or conditions in an effective manner. The term used herein "TGF-β-effective disorders or conditions" means disorders or conditions capable of being treated or prevented by natural-occurring TGF-β. The TGF-β-effective disorders or conditions are described in U.S. Pat. No. 5,780,436 and US Patent Application Publication No. 20020010134, the teachings of which are incorporated herein by reference.

According to a preferable embodiment, the composition of the present invention may has efficacies or activities on promotion of cell growth and division, physiological activities of epithelial cells, angiogenesis and neuron regeneration, tissue repair, wound healing, treatment of thrombosis, bone defects and atherosclerosis, biosynthesis of collagen, elastin, laminin and hyaluronic acid, treatment of periodontal diseases or improvement of skin conditions.

Where the present composition is applied to treatment of periodontal diseases, it may be formulated to provide toothpastes or compositions for tooth and mouth cleaning or care. The term "composition for treating periodontal diseases" may be interchangeably used herein with other terms, "composition for tooth and mouth care" and "composition for tooth and mouth cleaning". The peptide of this invention promotes biological activities of epithelial cells present in gum tissues and heals gum wound to regenerate damaged gum tissues, thereby treating or preventing periodontal diseases.

More preferably, the composition of the present invention has efficacies or activities on the improvement of skin conditions. First of all, the peptide used as an active ingredient in the present composition shows excellent skin permeation due to their low molecular weight. Accordingly, where the present composition is topically applied to skin, it becomes evident that skin conditions are considerably improved. Much more preferably, the improvement in the skin conditions by the present composition includes skin whitening, the improvement in wrinkle or skin elasticity, the prevention of skin aging, the improvement in skin moisture, the removal of dark spots, the treatment of acne, wound healing and skin regeneration, and most preferably, skin whitening and the improvement in wrinkle.

For example, the peptides used as an active ingredient in the present composition is able to exhibit superior efficacies on skin whitening by effectively blocking melanin biosynthesis (e.g., inhibition of tyrosinase activity), and on removal of wrinkle (e.g., induction of procollagen or fibronectin biosynthesis). The skin whitening composition of the present invention has remarkable effects on: (a) induction of bright skin tones; (b) maintenance of skin tones; and (c) removal of skin pigment or dark spots.

Moreover, the peptide of the present invention is expected to be actively applied as a therapeutic drug in highly safe manner because of its non-cytotoxicity to various human-derived cells.

The present composition may be prepared as a pharmaceutical or cosmetic composition.

According to a preferable embodiment, the composition is a pharmaceutical composition comprising (a) a pharmaceutically effective amount of the peptides of the present invention; and (b) a pharmaceutically acceptable carrier.

The term used herein "pharmaceutically effective amount" refers to an amount enough to show and accomplish efficacies and activities of the peptide of this invention.

The pharmaceutically acceptable carrier contained in the pharmaceutical composition of the present invention, which is commonly used in pharmaceutical formulations, but is not limited to, includes lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methylcellulose, methyl hydroxy benzoate, propylhydroxy benzoate, talc, magnesium stearate, and mineral oils. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in *Remington's Pharmaceutical Sciences* (19th ed., 1995), which is incorporated herein by reference.

The pharmaceutical composition according to the present invention may be administered orally or parenterally, and preferably, administered parenterally, e.g., by intravenous, subcutaneous, intramuscular, intraperitoneal, local or transdermal administration.

A suitable dosage amount of the pharmaceutical composition of the present invention may vary depending on pharmaceutical formulation methods, administration methods, the patient's age, body weight, sex, pathogenic state, diet, administration time, administration route, an excretion rate and sensitivity for a used pharmaceutical composition. Preferably, the pharmaceutical composition of the present invention may be administered with a daily dosage of 0.0001-100 μg.

According to the conventional techniques known to those skilled in the art, the pharmaceutical composition according to the present invention may be formulated with pharmaceutically acceptable carrier and/or vehicle as described above, finally providing several forms such as a unit dose form and a multi-dose form. Non-limiting examples of the formulations include, but not limited to, a solution, a suspension or an emulsion in oil or aqueous medium, an extract, an elixir, a powder, a granule, a tablet and a capsule, and may further comprise a dispersion agent or a stabilizer.

According to a preferable embodiment, the composition is a cosmetic composition comprising (a) a cosmetically effective amount of the peptide of the present invention; and (b) a cosmetically acceptable carrier.

The term used herein "cosmetically effective amount" refers to an amount enough to accomplish efficacies on improvements in skin conditions described hereinabove.

The cosmetic compositions of this invention may be formulated in a wide variety of forms, for example, including a solution, a suspension, an emulsion, a paste, an ointment, a gel, a cream, a lotion, a powder, a soap, a surfactant-containing cleanser, an oil, a powder foundation, an emulsion foundation, a wax foundation and a spray. Specifically, the cosmetic compositions of this invention may be formulated in the form of skin softner, nutrient liquid, nutrient cream, massage cream, essence, eye cream, cleansing cream, cleansing foam, cleansing water, pack, spray or powder.

Where the cosmetic composition is in the form of paste, cream or gel, it may comprise animal and vegetable fats, waxes, paraffins, starch, tragacanth, cellulose derivatives, polyethylene glycols, silicones, bentonites, silica, talc or zinc oxide.

In the formulation of powder or spray, it may comprise lactose, talc, silica, aluminum hydroxide, calcium silicate or polyamide powder. Spray may additionally comprise the customary propellants, for example, chlorofluorohydrocarbons, propane/butane or dimethyl ether.

The formulation of solution and emulsion may comprise solvent, solubilizer and emulsifier, for example water, ethanol, isopropanol, ethyl carbonate, ethyl acetate, benzyl alcohol, benzyl benzoate, propylene glycol, 1,3-butylglycol, oils, glycerol fatty esters, polyethylene glycol and fatty acid esters of sorbitan.

The formulation of suspension may comprise liquid diluents, for example water, ethanol or propylene glycol, suspending agents such as ethoxylated isosteary alcohols, polyoxyethylene sorbitol esters and poly oxyethylene sorbitan esters, micocrystalline cellulose, aluminum metahydroxide, bentonite, agar or tragacanth.

The formulation of cleansing compositions with surfactant may comprise aliphatic alcohol sulfate, aliphatic alcohol ether sulfate, sulfosucinnate monoester, isothinate, imidazolium derivatives, methyltaurate, sarcocinate, fatty acid amide ether sulfate, alkyl amido betain, aliphatic alcohol, fatty acid glyceride, fatty acid diethanolamide, vegetable oil, lanoline derivatives or ethoxylated glycerol fatty acid ester.

Furthermore, the cosmetic compositions of this invention may contain auxiliaries as well as peptides as active ingredients and carriers. The non-limiting examples of auxiliaries include antioxidants, stabilizers, solubilizers, vitamins, colorants and odor improvers.

BRIEF DESCRIPTION OF THE DRAWINGS

FIG. 1 represents the amino acid sequence of natural-occurring transforming growth factor-beta (TGF-β) and the peptide of the present invention.

Figure 2:
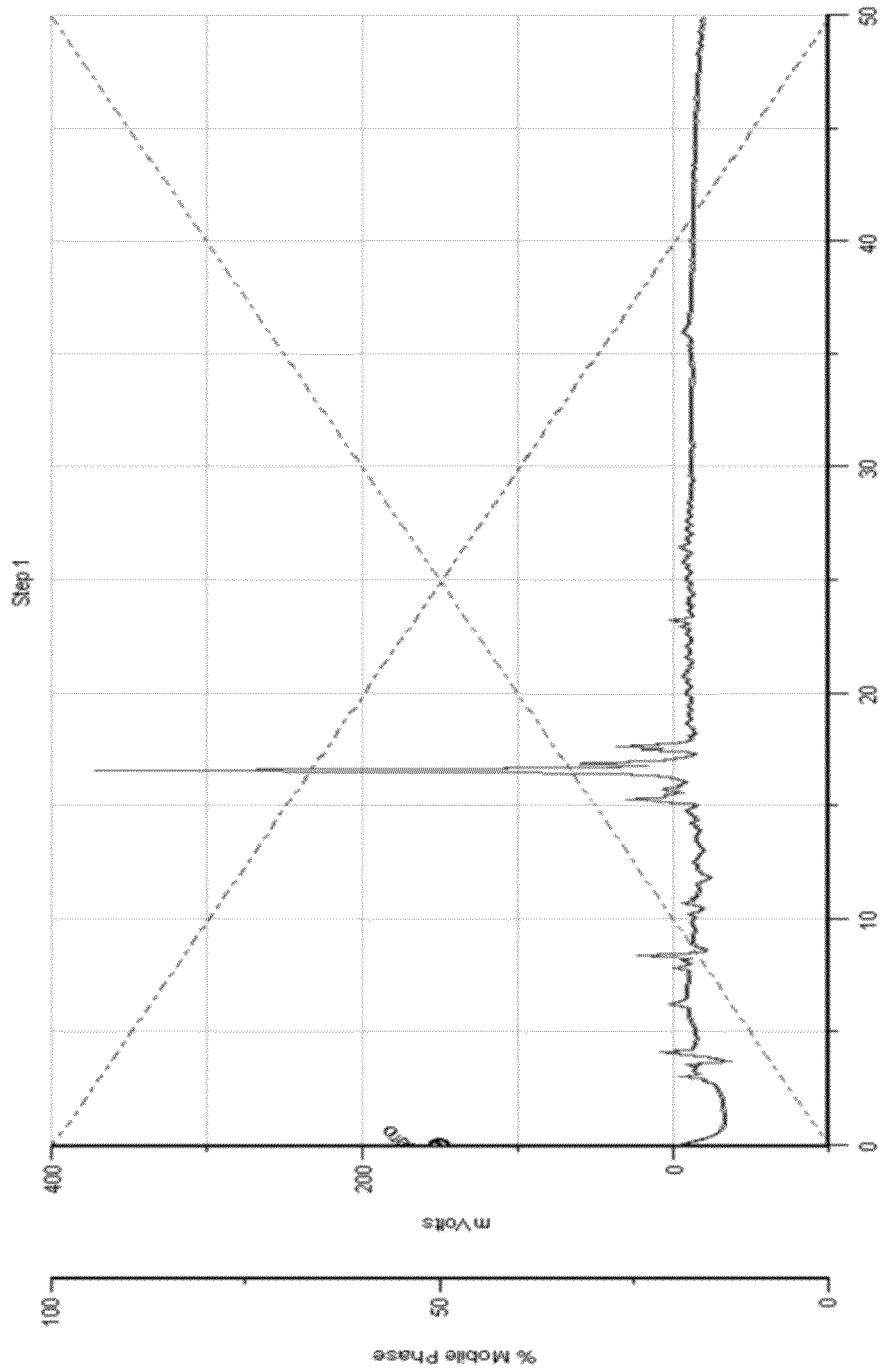
FIG. 2 represents a high performance liquid chromatography analysis of the peptide of SEQ ID NO:1 prepared in Example 1.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1

Synthesis of Peptide 2

500 mg of chloro trityl chloride resin (CTL resin, Nova Biochem Cat No. 01-64-0021) introduced into a reactor were added 10 ml of methylene chloride (MC) and agitated for 3 min. After removing solution, 10 ml of dimethylformamide (DMF) were added to the resultant and then agitation was carried out for 3 min, after which the solvent was removed. Ten ml of dichloromethane solution were added to the reactor and 200 μmole of Fmoc-Gln(trt)-OH (Novabiochem) and 400 μmole of diisopropyl ethylamine (DIEA) were then added to the reactor, after which the mixture was dissolved by agitation and reaction was then undertaken with agitating for 1 hr. After reaction, the resultant was washed and reacted for 10 min in methanol and DIEA (2:1) dissolved in DCM, followed by washing with excess DCM/DMF (1:1). After the removal of the solvent, 10 ml of DMF were added to the reactor and agitated for 3 min, followed by removing the solvent. Ten ml of a deprotection solution (20% piperidine/DMF) were added to the reactor and agitated for 10 min at room temperature, and solution removal was performed. After adding the same volume of the deprotection solution, the reaction was undertaken for 10 min and solution was removed, followed by washing sequentially with DMF (twice), MC and DMF to yield Gln-(trt)-CTL resins. Ten ml of DMF solution was added to a new reactor and then 200 μmole of Fmoc-Thr(otbu)-OH (Novabiochem), 200 μmole of HoBt (N-Hydroxybenzotriazole) and 200 μmole of Bop were added, followed by agitation for solubilization. 400 μmole of DIEA was added to the reactor twice as a fraction and agitation was carried out for at least 5 min to dissolve all solid contents. The dissolved amino acid solution was introduced into the reactor containing the deprotected resin and reaction was undertaken with agitating for 1 hr at room temperature. Following the removal of the reaction solution, the resultant was agitated three times with DMF solution for 5 min to remove unreacted residuals. A small amount of the reacted resin was taken to evaluate extent of reactions by Ninhydrine test. Using the deprotection solution, the deprotection was performed twice in the same manner as described above to yield Thr(otbu)-Gln(trt)-CTL resins. After sufficiently washing with DMF and MC, Ninhydrine test was carried out again and then the attachments of amino acids were performed as described below. Based on the amino acid sequence depicted in FIG. 1, Fmoc-Asp(otbu), Fmoc-Leu, Fmoc-Ser(tBu), Fmoc-Trp(boc), Fmoc-Ile, Fmoc-Thr(tBu), Fmoc-Asp(otbu), Fmoc-Gly, Fmoc-Arg(pbf), Fmoc-Gly were sequentially attached to the resins. After removing Fmoc-protecting group by incubating with the deprotection solution as described above, the prepared peptidyl resins were washed three times sequentially with DMF, MC and methanol, dried under the flow of nitrogen gas, completely dried by vacuum-drying under $P_2O_5$ and then reacted with 30 ml of the leaving solution [containing 81.5% TFA (trifluroacetic acid), 5% distilled water, 5% thioanisole, 5% phenol, 2.5% EDT and 1% TIS] for 2 hr at room temperature upon intermittent agitating. The resin was filtered and washed with a small volume of TFA solution, after which the filtrate was combined with the mother liquor. After distillation under reduced pressure to reduce the total volume by two, the precipitation was induced using 50 ml of cold ether and the formed precipitates were collected by centrifugation, followed by washing twice with cold ether. After removing the mother liquor, the resultant was completely dried under nitrogen atmosphere to provide 0.144 g of unpurified peptide 2 of SEQ ID NO:1, $NH_2$-Gly-Arg-Gly-Asp-Tyr-Ile-Trp-Ser-Leu-Asp-Thr-Gln-OH. The molecular weight of the final product was determined as 1411.0 (theoretical MW 1410.5) using a mass analyzer.

FIG. 2 is a high performance liquid chromatography analysis of the peptide of SEQ ID NO:1 prepared in Example.

Example 2

Heat Stability of the Prepared Peptide

To evaluate heat stability of the peptide 2 prepared in Example 1, the peptide 2 was dissolved in 50 mM Tris-HCl buffer (pH 8.0) to a concentration of 10 μg/ml. Recombinant TGF-β1 (Sigma) as control was produced from *E. coli* and dissolved in 50 mM Tris-HCl buffer (pH 8.0) at a concentration of 1 μg/ml. The prepared solutions were introduced into glass vials and kept to stand at 40° C. Afterwards, the solutions were taken on days 0, 1, 10, 25, 50, 75 and 100, and subjected to MTT assay (Scudiero, D. A., et al., *Cancer Res.*, 48: 4827-4833 (1988)) to determine residual activities of the peptide and recombinant TGF-β1 (FIG. 3).

Figure 3:
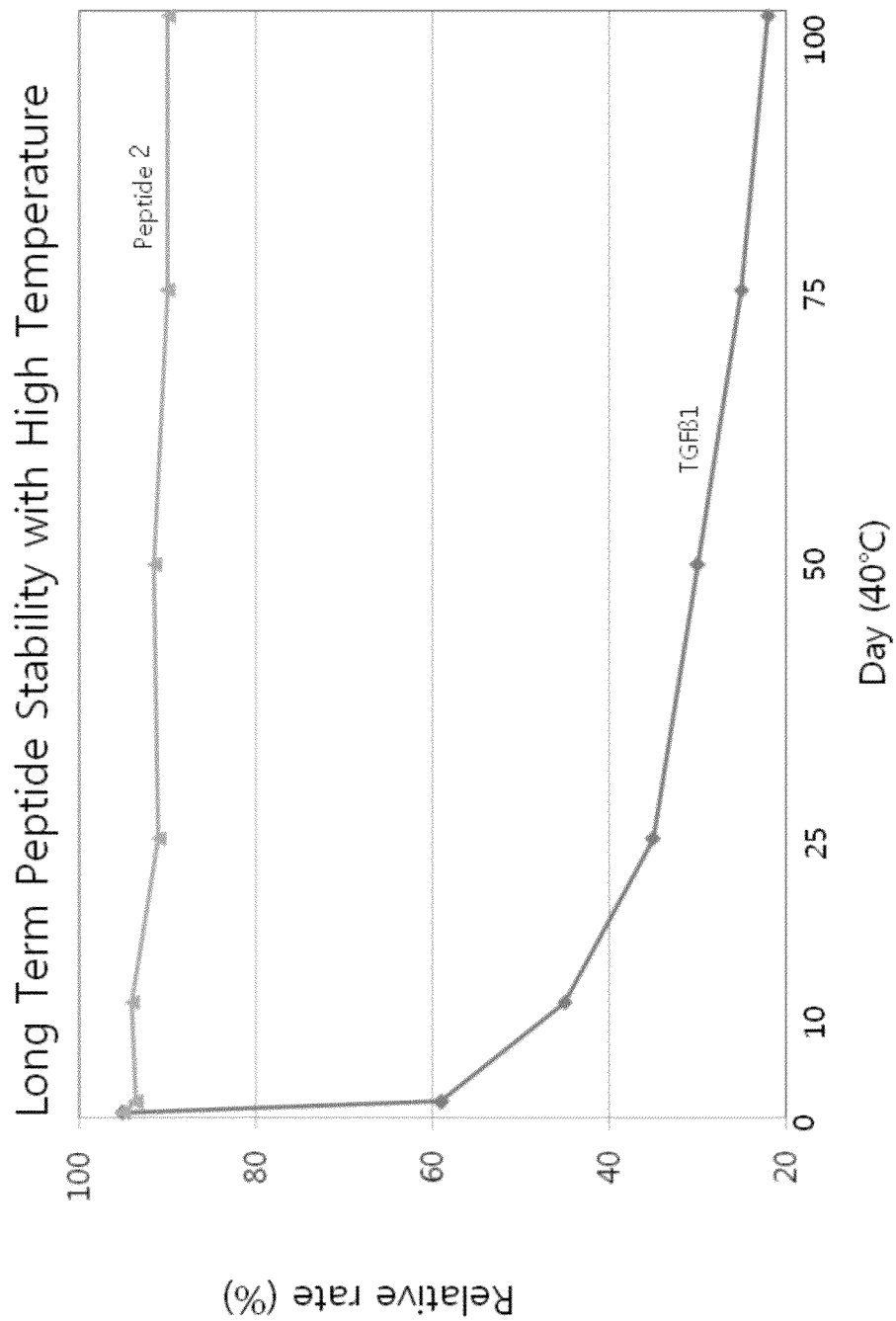
FIG. 3 is a graph comparing heat stability of the peptides of the present invention with that of natural-occurring TGF-β.

As shown in FIG. 3, the activity of the recombinant TGF-β1 protein was sharply decreased with the lapse of time. In contrast, the activity of the present peptide was shown not to be decreased over time.

Example 3

Preparation of Nano Peptide 50 mg of the peptide synthesized in Example 1 above was dissolved in 500 ml of distilled water by vigorous agitation. The peptide solution was mixed with 5 g lecithin, 0.3 ml sodium oleate, 50 ml ethanol and a small amount of oils, and its volume was adjusted with distilled water to 1 L. The resulting solution was subjected to a microfluidizer under high pressure for emulsification, thereby providing nanosomes having 100-nm size. The nanosomes were prepared to have a final concentration of about 50 ppm and used as ingredients for cosmetics in alone or combination with others.

Formulation Example 1

Preparation of Skin Softner

A skin softner containing one or more peptide nanosomes prepared in Example 1 was formulated according to the following composition:

TABLE 1

| Ingredients | Content (wt %) |
| --- | --- |
| Peptide nanosomes (SEQ ID NO: 1) | 0.001 |
| 1,3-butylene glycol | 6.0 |
| Glycerin | 4.0 |
| PEG 1500 | 1.0 |
| Sodium hyaluronate | 1.0 |
| Polysorbate 20 | 0.5 |
| Ethanol | 8.0 |
| Preservative, pigment | Proper amount |
| Benzophenone-9 | 0.05 |
| Perfume | Minute amount |
| Distilled water | Residual amount |
| Total | 100 |

Formulation Exmaple 2

Preparation of Nutrient Cream

A nutrient cream containing one or more peptide nanosomes prepared in Example 1 was formulated according to the following composition:

TABLE 2

| Ingredients | Content (wt %) |
| --- | --- |
| Peptide nanosomes (SEQ ID NO: 1) | 0.001 |
| Meadowfoam oil | 3.0 |
| Cetearylalcohol | 1.5 |
| Stearic acid | 1.5 |
| Glyceryl stearate | 1.5 |
| Liquid paraffin | 10.0 |
| Wax | 2.0 |
| Polysorbate 60 | 0.6 |
| Sorbitan sesquiolate | 2.5 |
| Squalane | 3.0 |
| 1,3-butylene glycol | 3.0 |
| Glycerine | 5.0 |
| Triethanol amine | 0.5 |
| Tocopheryl acetate | 0.5 |
| Preservative, pigments | Proper amount |
| Perfume | Proper amount |
| Distilled water | Residual amount |
| Total | 100 |

Formulation Example 3

Nutrient Liquid

A nutrient liquid containing one or more peptide nanosomes prepared in Example 1 was formulated according to the following composition:

TABLE 3

| Ingredients | Content (wt %) |
| --- | --- |
| Peptide nanosomes (SEQ ID NO: 1) | 0.002 |
| 1,3-butylene glycol | 4.0 |
| Glycerin | 4.0 |
| Cetearyl alcohol | 0.8 |
| Glyceryl stearate | 1.0 |
| Triethanol amine | 0.13 |
| Tocopheryl acetate | 0.3 |
| Liquid paraffin | 5.0 |
| Squalane | 3.0 |
| Makadamianut oil | 2.0 |
| Polysorbate 60 | 1.5 |
| Sorbitan sesquiolate | 0.5 |
| Carboxyvinyl polymer | 1.0 |
| Preservative, pigments | Proper amount |
| Perfume | Proper amount |
| Distilled water | Residual amount |
| Total | 100 |

Formulation Example 4

Preparation of Essence

An essence containing one or more peptide nanosomes prepared in Example 1 was formulated according to the following composition:

TABLE 4

| Ingredients | Content (wt %) |
| --- | --- |
| Peptide nanosomes (SEQ ID NO: 1) | 0.005 |
| Glycerin | 10.0 |
| 1,3-butylene glycol | 5.0 |
| PEG 1500 | 2.0 |
| Allantoin | 0.1 |
| DL-panthenol | 0.3 |
| EDTA-2Na | 0.02 |
| Hydroxyethyl cellulose | 0.1 |
| Sodium hyaluronate | 8.0 |
| Carboxyvinyl polymer | 0.2 |
| Triethanol amine | 0.18 |
| Octyldodeceth-16 | 0.4 |
| Ethanol | 6.0 |
| Perfume, preservative, pigments | Proper amount |
| Distilled water | Residual amout |
| Total | 100 |

Example 4

Melanin Pigment Decrease by the Present Peptide

Figure 4:
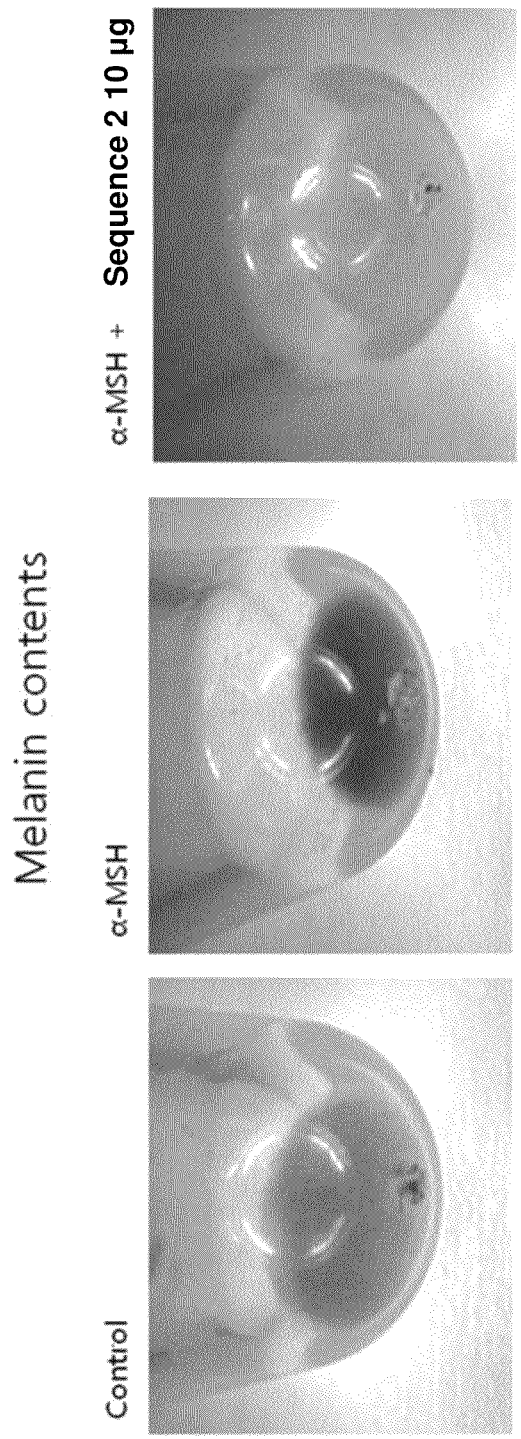
FIG. 4 shows an inhibitory effect on melanin generation in α-MSH-treated B16 melanoma after treatment with the present peptide prepared in Example 1.

To evaluate reduction of melanin pigment by the peptide 2 synthesized in Example 1, C57BL/6 Mice melanocytes cultured were incubated with α-MSH (melanocyte stimulating hormone; Sigma) and then with the peptide in the determined concentrations to measure inhibition effects on melanin generation. Mice melanocytes were cultured in DMEM (Dulbecco's modified Eagle's media; Sigma) supplemented with 10% FBS (fetal bovine serum; Sigma) at 37° C. under 5% $CO_2$ conditions. Cells were cultured in a 24-well culture plate with a density of $1 \times 10^5$ cells/well and their adhesion to the plate was observed. Then, cells were incubated with each test group for 3 days: (a) a solvent as control; (b) 200 μg/ml α-MSH as a positive control; and (c) 200 μg/ml α-MSH plus 1 μg/ml or 10 μg/ml peptide 2. The test materials were prepared in such a manner that each component was dissolved in medium solvent and diluted at an equivalent rate to the aforementioned concentration using a mixed solvent of propylene glycol:ethanol:distilled water (5:3:2). After removing culture medium by centrifugation, melanin contents in each group could be observed with naked eye. Of them, peptide 2 (10 µg/ml)-treated group was shown in FIG. 4. As illustrated in FIG. 4, melanin content in α-MSH-treated group was strikingly increased and melanin content in peptide 2-treated groups was similar to that of control. Accordingly, it could be appreciated that where a factor inducing melanin generation is applied to the skin, the peptide of the present invention may contribute to maintain bright skin tones by inhibiting its activity.

Figure 5:
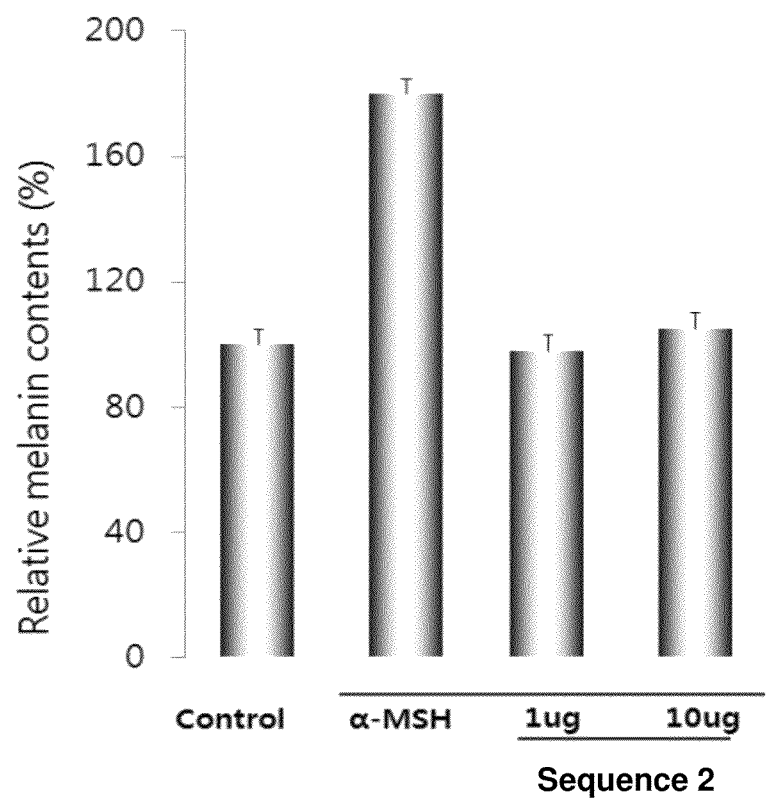
FIG. 5 is a graph to examine relative melanin contents in α-MSH-treated B16 melanoma by measuring absorbance at 400 nm using a spectrophotometer after treatment with the present peptide prepared in Example 1.

More specifically, cells were washed with PBS (phosphate buffered saline) and treated with 1 N sodium hydroxide. The resultants were analyzed to measure their absorbance values at 400 nm. The measured inhibition in melanin generation (Dooley method) was shown in FIG. 5. The result in FIG. 5 is consistent with that in FIG. 4.

Example 5

Inhibition of Tyrosinase Activity by the Present Peptide

For verifying effects on skin whitening of the peptide synthesized in Example 1 and TGF-β, cells were treated with α-MSH and the inhibition in melanin generation was measured. B16F10 cells (Korean Cell Line Bank) were inoculated in a density of $1\times10^5$ cells/well and cultured in DMEM for 3 days. After cell adhesion was observed, medium was changed with a fresh medium containing 2% serum. Cells were incubated with each test group for 4 days: (a) no treatment as negative control; (b) 200 µg/ml α-MSH as a positive control; and (c) 200 µg/ml α-MSH plus 1 µg/ml or 10 µg/ml peptide 2. Afterwards, cell morphology was observed in each group. Subsequently, cells were harvested and treated with a lysis buffer to extract total proteins. The extracted proteins were quantitated by the BCA (bicinchonic acid) method. For each experiment group, 90 µl of protein solution and 10 µl of L-DOPA (L-3,4-dihydroxyphenylalanine; Sigma) were added and reacted for 30 min at 37° C. The resultants were analyzed to measure their absorbance values at 405 nm for evaluating tyrosinase activities.

Figure 6:
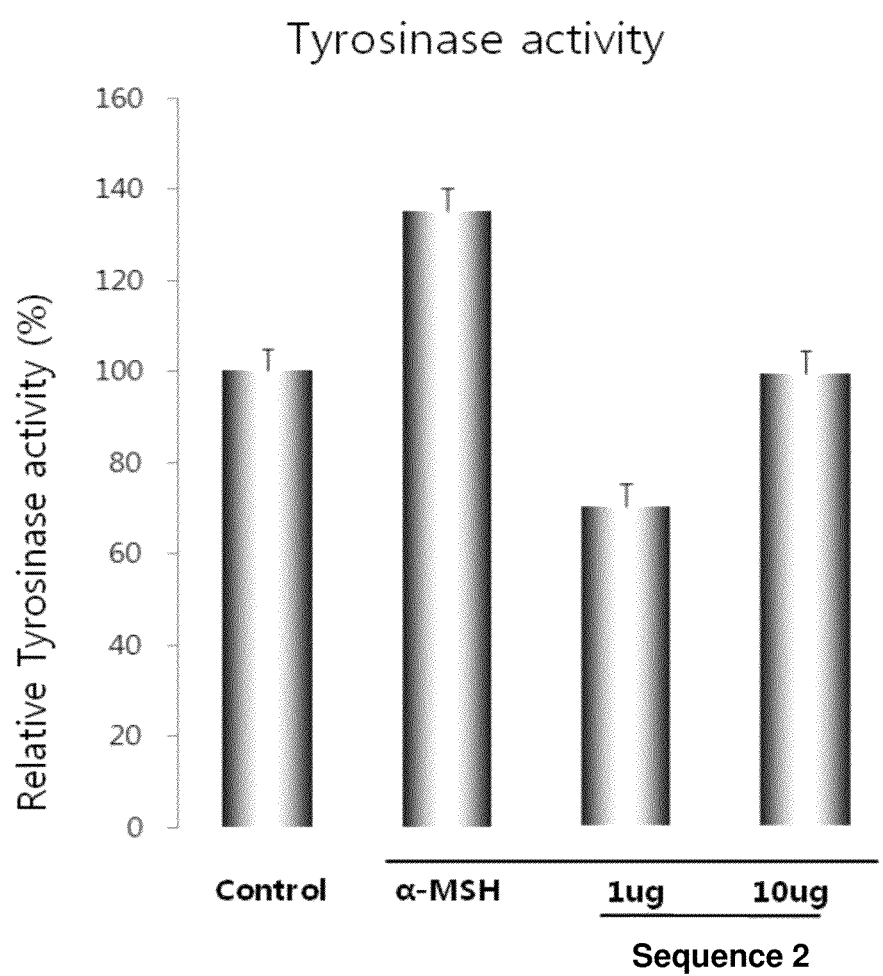
FIG. 6 is a graph to measure relative tyrosinase activity in α-MSH-treated B16 melanoma after treatment with the present peptide prepared in Example 1.

As represented in FIG. 6, the group treated with only α-MSH shows highly elevated level of tyrosinase activity. In contrast, the group treated with the peptide represents remarkably reduced tyrosinase activity (about 30% less than). The tyrosinase activity is represented as a relative value compared with peptide amount. As described above, it would be understood that where a factor elevating tyrosinase activity is applied to the skin, the peptide of the present invention may contribute to maintain bright skin tones by inhibiting tyrosinase activity and have its action mechanism identical to that of natural-occurring TGF-β.

Example 6

Inhibition of Tyrosinase Activity by the Present Peptide

To more clearly check activities of TGF-mimicking peptide on skin whitening in α-MSH-treated B16F10 melanoma cells, mRNA level of TRP1 (tyrosinase-related protein-1), TRP2 and MITF (microphthalmia-associated transcription factor) was measured using RT-PCR.

Figure 7:
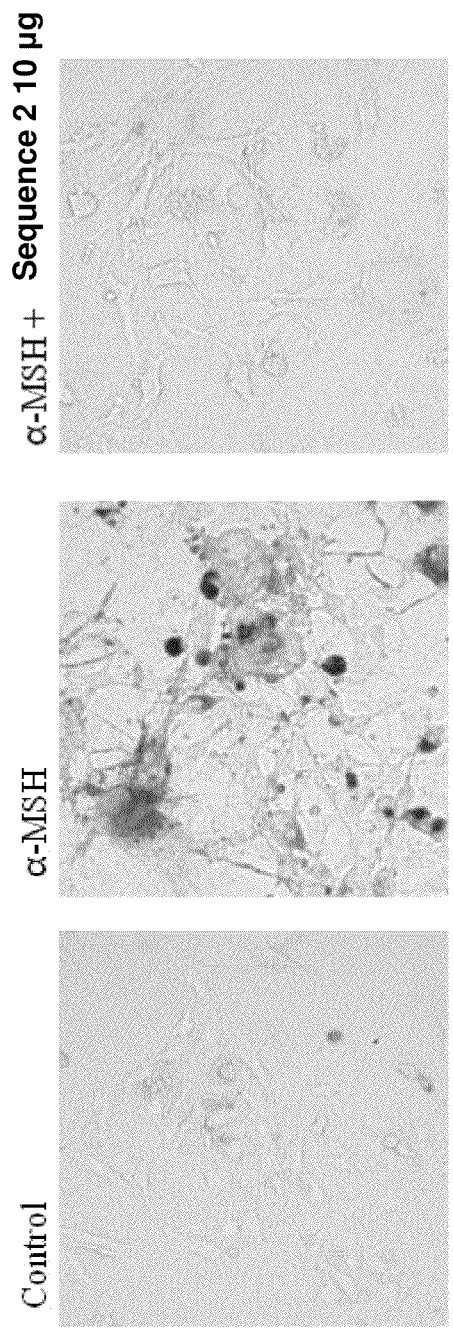
FIG. 7 shows an image to observe melanosome changes in α-MSH-treated B16 melanoma after treatment with the present peptide prepared in Example 1.

First, B16F10 cells were plated at a 6-well plate in a density of $1\times10^5$ cells/well and cultured for 3 days. After cell adhesion was observed, medium was changed with a fresh medium containing 2% serum. Cells were incubated with each test group for 4 days: (a) no treatment as negative control; (b) 200 µg/ml α-MSH as a positive control; and (c) 200 µg/ml α-MSH plus 10 µg/ml peptide 2. Afterwards, cell morphology was observed in each group. As shown in FIG. 7, α-MSH-induced melanosomes were eliminated by the present peptide 2.

Subsequently, mRNA were extracted from cells and RT-PCR was carried out using primers for TRP1, TRP2 and MITF. The primer sequence is as follows: TRP1 F-primer, 5'-GACAGACCGCTGTGGCTCAT-3' and TRP1 R-primer, 5'-CTCCAGACGCAGGAGGTGGTA-3'; TRP2 F-primer, 5'-GCATGACGGTGGACAGCCTAGT-3' and TRP2 R-primer, 5'-GTGTGGTGATCACGTAGTCGG-3'; and MITF F-primer, 5'-CCAGCCTGGCGATCATGTCATGC-3' and MITF R-primer, 5'-GGTTGGCTGGACAGGAGT-TGCTG-3'.

Figure 8:
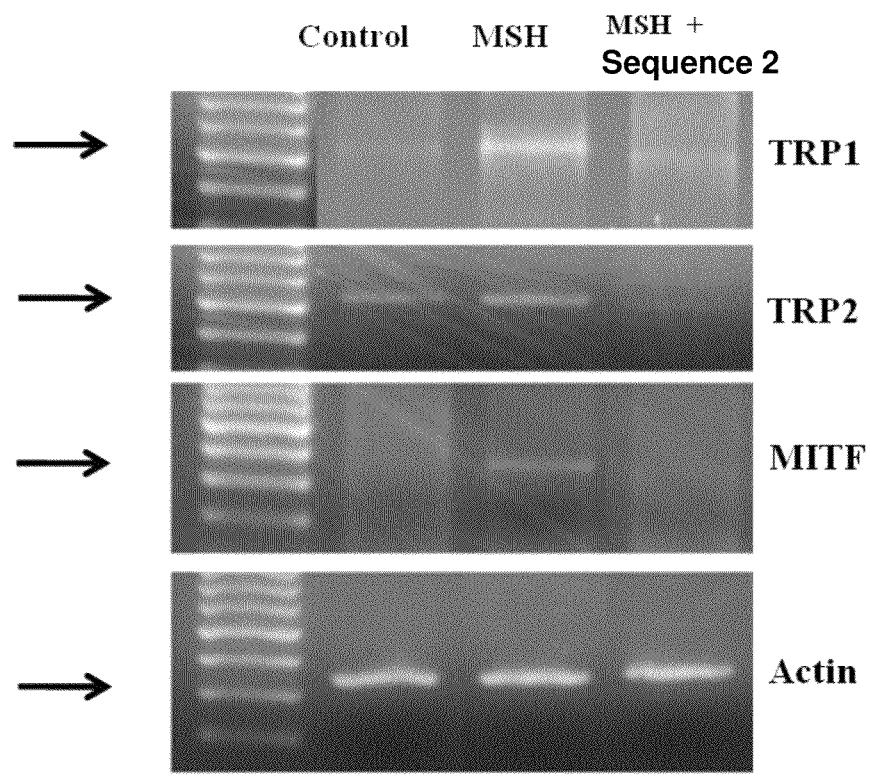
FIG. 8 is RT-PCR (reverse transcription-polymerase chain reaction) analysis, representing that expression of biomarkers involved in melanin synthesis are reduced in α-MSH-treated B16 melanoma by treatment with the present peptide prepared in Example 1.

As a result, it was illustrated that the peptide of the present invention permits to inhibit mRNA level of TRP1, TRP2 and MITF (FIG. 8).

Example 7

Figure 9:
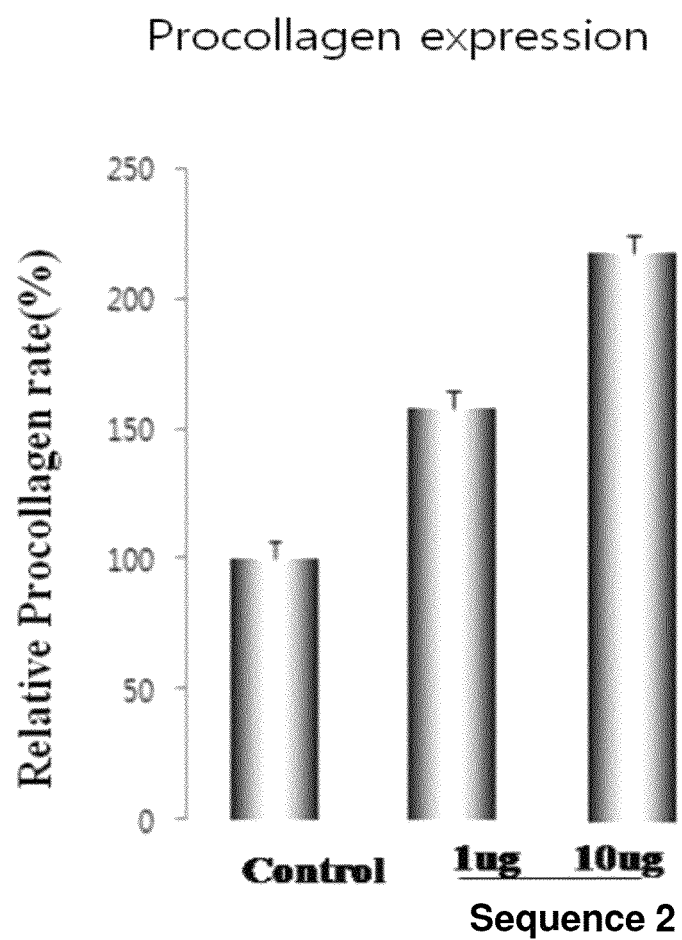
FIG. 9 represents a graph to show elevated procollagen expression in NIH3T3 fibroblasts incubated with the peptide of this invention.
Figure 10:
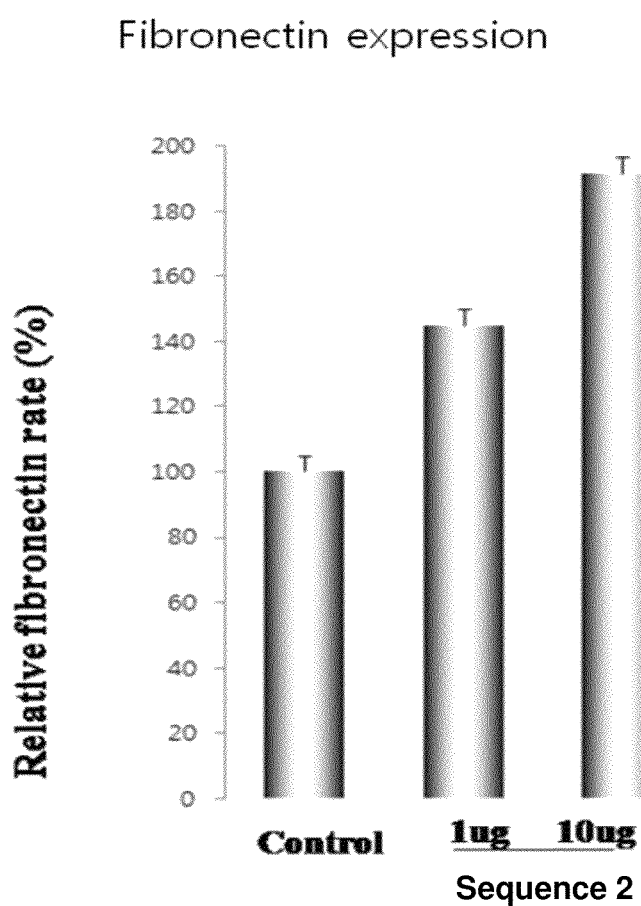
FIG. 10 represents a graph to show elevated fibronectin expression in NIH3T3 fibroblasts incubated with the peptide of this invention.

Stimulatory Effects of the Present Peptide on Production of Procollagen and Fibronectin NIH3T3 cells cultured for 48 hr were incubated with the peptide of the present invention with a concentration of 1 µg/ml or 10 µg/ml for 72 hr, respectively. The levels of procollagen and fibronectin, indicators to show the improvement in skin wrinkle, were examined. The quantification was performed using Procollagen ELISA kit (Takara, Japan) and Fibronectin ELISA kit (CHEMICON, USA). As shown in FIG. 9, the peptide of the present invention was revealed to elevate the level of procollagen in fibroblasts. First of all, the peptide 2 of the present invention was shown to remarkably promote the production of procollagen. In addition, as demonstrated in FIG. 10, the peptide of the present invention was found to increase the level of fibronectin in fibroblasts. Especially, the peptide 2 of the present invention was revealed to strikingly facilitate the production of procollagen.

Taken together, these results demonstrate that the peptide of the present invention has highly excellent effects on the improvement in skin conditions.

Example 8

Cytotoxicity of the Present Peptide

To verify cytotoxicity of the peptide of this invention on skin cells, SRB (Sulforhodamine B; Sigma) colorimetric assay was carried out using HaCaT (Korean Cell Line Bank), NIH3T3 (Korean Cell Line Bank) and B16F10 (Korean Cell Line Bank) cells according to Rizzino et al. method (Rizzino, et al., *Cancer Res.*, 48: 4266 (1988)). HaCaT, NIH3T3 or B16F10 cells were cultured in 250 ml-flasks containing EMEM (Eagle's minimal essential media; Gibco, U.S.A.) supplemented with 10% FBS, respectively. Cells cultured were treated with 0.25% trypsin solution to detach cells from the bottom of culture flasks and centrifuged to collect cell pellets. After cell pellets were resuspended in a fresh EMEM without FBS, its aliquot ($1\times10^5$) cells was added to each well of 96-well plates and cultured for 24 hr at 37° C. under 7% $CO_2$. And then, the medium was changed with a fresh serum-depleted medium. For standardization, control and peptide was dissolved in water and 10% DMSO (dimethyl sulfoxide) in sterilized conditions. Afterwards, cells were incubated with the peptide (10 ng/ml, 100 ng/ml, 1 μg/ml, 10 μg/ml and 100 μg/ml) dissolved in 10% DMSO for 72 hr under the same conditions as described above. After removing supernatants, cells were washed once using PBS and incubated with SRB solution (Sigma). Cells were sufficiently washed with PBS and observed under a microscope to find cell viability. In addition, absorbance at 590 nm was measured to analyze cell proliferation (FIGS. 11a-11c).

Figure 11A:
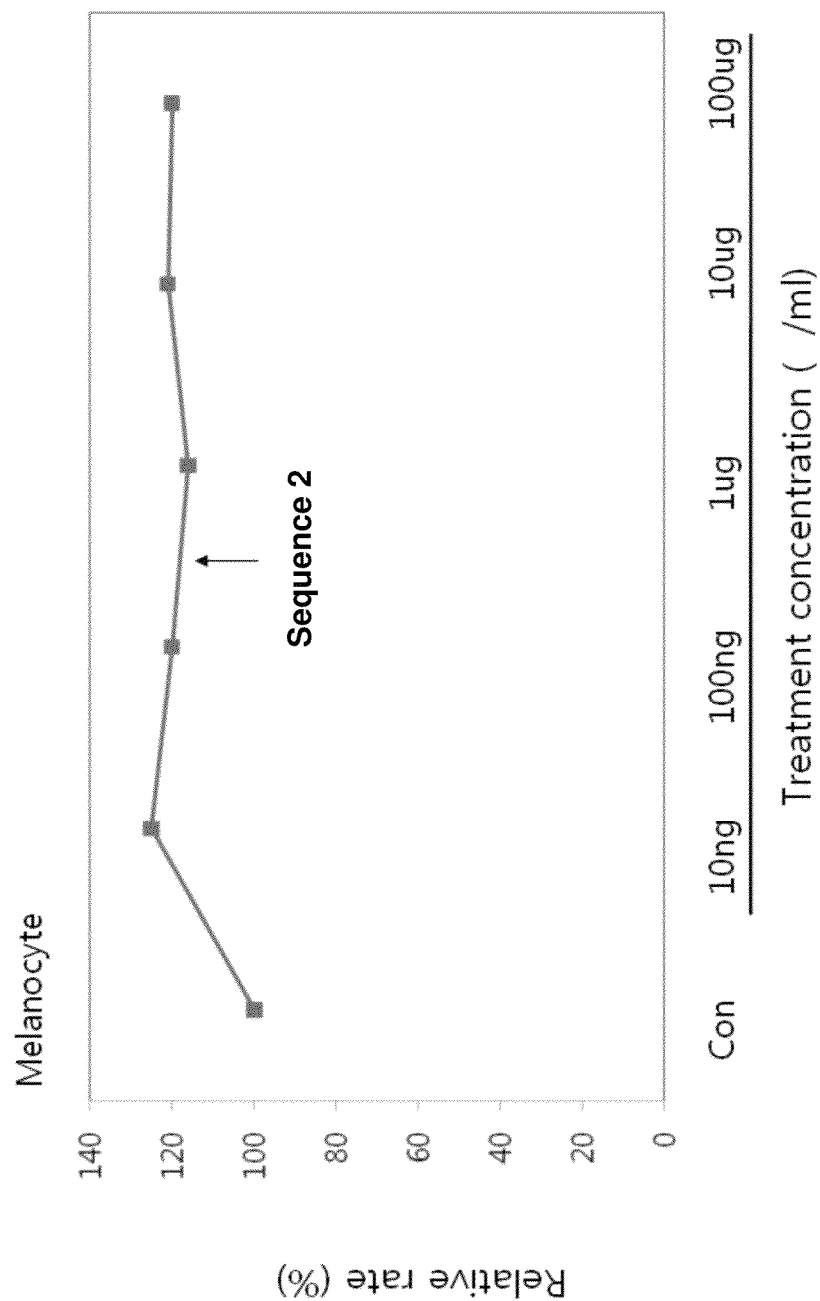
FIGS. 11a-11c are results to test a cytotoxicity of the present peptide to HaCat keratinocyte cell line HaCaT, fibroblast cell line NIH3T3 and melanocyte cell line B16F10.
Figure 11B:
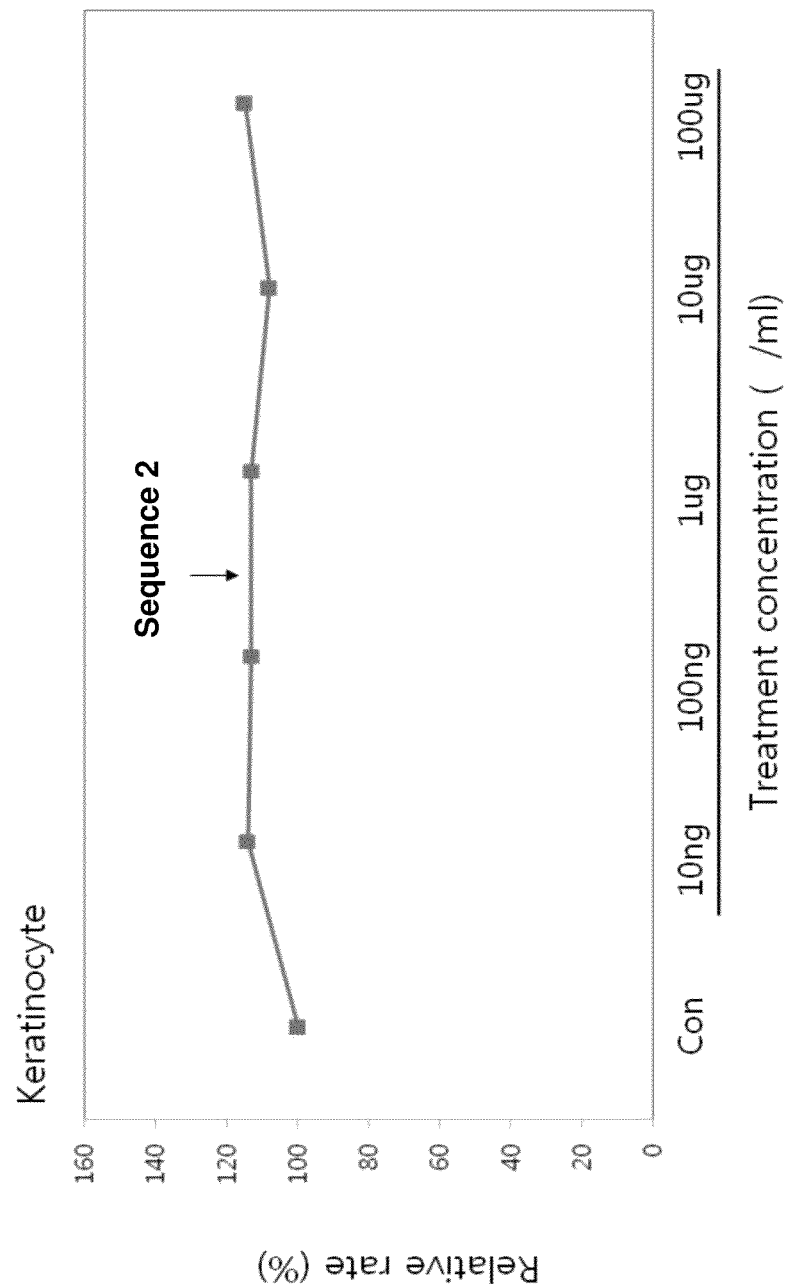
Figure 11C:
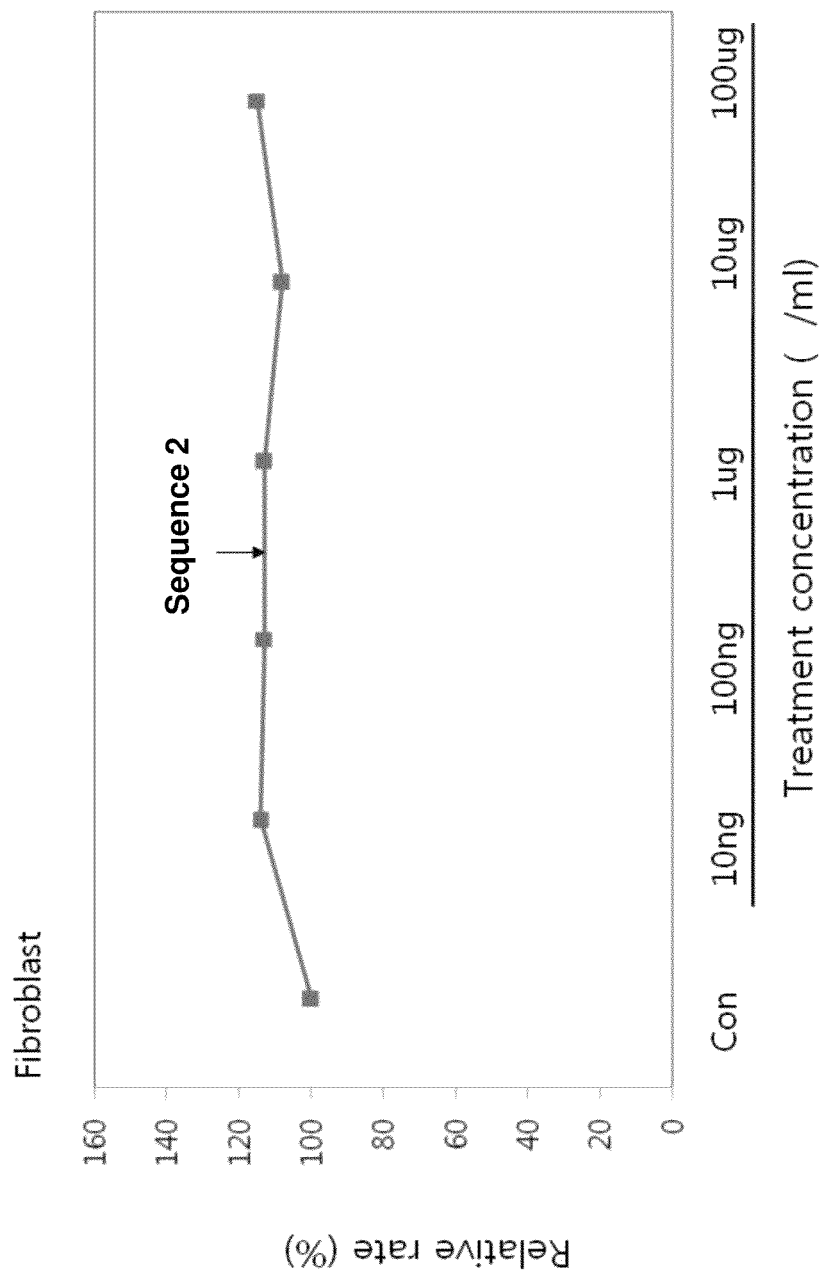

As represented in FIGS. 11a-11c, the decrease in cell number and changes of cell morphology were not shown in HaCaT, NIH3T3 and B16F10 cells at all concentrations (i.e., low and high concentration) of the peptide under microscope. These results address that the peptide of the present invention induce little or no adverse effects on skin cells.

The features and advantages of the present invention will be summarized as follows:

(i) the peptide of the present invention is derived from human TGF-β and possess identical functions or activities to natural-occurring human TGF-β;

(ii) the peptide of the present invention may be much higher stability than natural-occurring TGF-β and improve drawbacks caused by high molecular weight of natural-occurring TGF-β; and (iii) the peptide of this invention can be advantageously applied to treatment or improvement of TGF-β-effective disorders or conditions and have excellent efficacies on skin whitening and wrinkle improvement.

Having described a preferred embodiment of the present invention, it is to be understood that variants and modifications thereof falling within the spirit of the invention may become apparent to those skilled in this art, and the scope of this invention is to be determined by appended claims and their equivalents.

2. The TGF-β-mimicking peptide according to claim 1, wherein the cell adhesion amino acid sequence is RGD(Arg-Gly-Asp), RGDS(Arg-Gly-Asp-Ser), RGDC(Arg-Gly-Asp-Cys), RGDV(Arg-Gly-Asp-Val), RGES(Arg-Gly-Glu-Ser), RGDSPASSKP(Arg-Gly-Asp-Ser-Pro-Ala-Ser-Ser-Lys-Pro), GRGDS(Gly-Arg-Gly-Asp-Ser), GRADSP(Gly-Arg-Ala-Asp-Ser-Pro), KGDS(Lys-Gly-Asp-Ser), GRGDSP (Gly-Arg-Gly-Asp-Ser-Pro), GRGDTP(Gly-Arg-Gly-Asp-Thr-Pro), GRGES(Gly-Arg-Gly-Glu-Ser), GRGDSPC(Gly-Arg-Gly-Asp-Ser-Pro-Cys), GRGESP(Gly-Arg-Gly-Glu-Ser-Pro), SDGR(Ser-Asp-Gly-Arg), YRGDS(Tyr-Arg-Gly-Asp-Ser), GQQHHLGGAKQAGDV (Gly-Gln-Gln-His-His-Leu-Gly-Gly-Ala-Lys-Gln-Ala-Gly-Asp-Val), GPR (Gly-Pro-Arg), GHK(Gly-His-Lys), YIGSR(Tyr-Ile-Gly-Ser-Arg), PDSGR(Pro-Asp-Ser-Gly-Arg), CDPGYIGSR (Cys-Asp-Pro-Gly-Tyr-Ile-Gly-Ser-Arg), LCFR(Leu-Cys-Phe-Arg), EIL(Glu-Ile-Leu), EILDV(Glu-Ile-Leu-Asp-Val), EILDVPST(Gludle-Leu-Asp-Val-Pro-Ser-Thr), EILEVPST (Gludle-Leu-Glu-Val-Pro-Ser-Thr), LDV(Leu-Asp-Val) or LDVPS(Leu-Asp-Val-Pro-Ser).

3. The TGF-β-mimicking peptide according to claim 2, wherein the cell adhesion amino acid sequence is RGD(Arg-Gly-Asp).

4. The TGF-β-mimicking peptide according to claim 1, wherein the N-terminal or C-terminal of the peptide is further protected with a protection group selected from the group consisting of acetyl group, fluorenyl methoxy carbonyl group, formyl group, palmitoyl group, myristyl group, stearyl group, polyethylene glycol (PEG) and an amino acid.

5. The peptide according to claim 4, wherein the protection group is linked to the N-terminal of the peptide.

6. A method for prevention or treatment of TGF-β-effective disorders or conditions, comprising administering to a sub-

What is claimed is:

1. A TGF-β (transforming growth factor-beta)-mimicking peptide, wherein the amino acid sequence of said peptide consists of the amino acid sequence represented by SEQ ID NO:1 and a cell adhesion amino acid sequence linked to the N-terminal end of SEQ ID NO:1.

ject in need thereof a composition which comprises as an active ingredient the peptide having activities of TGF-β according to claim 1.

7. The method according to claim 6, wherein the TGF-β-effective disorders or conditions comprise tissue injury, atherosclerosis, wound, bone defects, rheumatoid arthritis, uveitis, cancers, wrinkle improvement or skin whitening.

* * * * *

```
                    SEQUENCE LISTING

<160> NUMBER OF SEQ ID NOS: 2

<210> SEQ ID NO 1
<211> LENGTH: 8
<212> TYPE: PRT
<213> ORGANISM: Artificial Sequence
<220> FEATURE:
<223> OTHER INFORMATION: TGF-Beta Mimicking Peptide 1

<400> SEQUENCE: 1

Tyr Ile Trp Ser Leu Asp Thr Gln
1               5

<210> SEQ ID NO 2
<211> LENGTH: 12
<212> TYPE: PRT
<213> ORGANISM: Artificial Sequence
<220> FEATURE:
<223> OTHER INFORMATION: TGF-Beta Mimicking Peptide 2

<400> SEQUENCE: 2

Gly Arg Gly Asp Tyr Ile Trp Ser Leu Asp Thr Gln
1               5                   10
```